United States Patent [19]

Szturma

[11] 4,150,123

[45] Apr. 17, 1979

[54] METHOD FOR TREATING GASTRO INTESTINAL ULCERS WITH EXTRACT OF HERB CETRARIA

[76] Inventor: Wladyslaw Szturma, 300 N. Lincoln Ave., Vineland, N.J. 08360

[21] Appl. No.: 853,152

[22] Filed: Nov. 21, 1977

[51] Int. Cl.² .................... A61K 35/78; A61K 31/70
[52] U.S. Cl. .................................. 424/195; 424/180
[58] Field of Search .................... 424/195, 34, 35, 180

[56] References Cited

U.S. PATENT DOCUMENTS

| 47,750 | 5/1865 | Schultz | 424/195 |
|---|---|---|---|
| 102,833 | 5/1870 | Kessler | 424/180 |
| 957,204 | 5/1910 | Gariscan | 424/195 |
| 2,095,259 | 10/1937 | Kober et al. | 424/180 |

OTHER PUBLICATIONS

National Dispensatory 1879, P.T.O. Lib. (RS 1512N7), pp. 380 and 381.

*Primary Examiner*—Donald B. Moyer
*Attorney, Agent, or Firm*—Michael F. Petock

[57] ABSTRACT

A pharmaceutical preparation for treating gastro intestinal ulcers, and particularly ulcers of the stomach and duodenum, is produced as an alcohol extract of the herb Cetraria, also known as Iceland Moss and by the Latin name Cetraria Islandica. The extract is preferably derived from the herb Cetraria by a strong grain or ethyl alcohol solvent. The alcohol extract is administered orally and has been found to be effective to treat ulcers of the stomach and duodenum.

2 Claims, No Drawings

METHOD FOR TREATING GASTRO INTESTINAL ULCERS WITH EXTRACT OF HERB CETRARIA

DESCRIPTION OF THE INVENTION

The present invention relates to a pharmaceutical preparation and a method for treating gastro intestinal ulcers, and particularly ulcers of the stomach and/or the duodenum. More particularly, the present invention relates to an alcohol extract of the herb Cetraria and the use of the herb Cetraria in a method for treating ulcers of the gastro intestinal tract, and particularly those of the stomach and/or duodenum.

There are in excess of 15 million people in the United States presently suffering from ulcers of the gastro intestinal tract. As of the present time, there is no known cure for ulcers in the stomach and duodenum. Where these ulcers have been treated to some extent by dieting and other medicinal preparations, the ulcers have reoccurred. In the past, dieting and surgery have often been used to treat ulcers of the stomach and duodenum without great success.

In accordance with the present invention, it was discovered that a pharmaceutical preparation prepared as an extract of the plant Cetraria was highly effective in treating ulcers in the gastro intestinal tract, and particularly in the stomach and duodenum. Although it is common for ulcers of the stomach and/or duodenum to reoccur, particularly in the beginning of spring and autumn, there was no known reoccurrence of pain and suffering of the ulcers after being treated by the pharmaceutical preparation of the present invention.

In accordance with the present invention, the pharmaceutical preparation is made by making an extract of the herb or plant Cetraria. Cetraria is also known by the names Iceland Moss and the Latin name Cetraria Islandica. Cetraria is a foliaceous lichen found in cool damp places in Europe, Great Britain, Iceland and the northern parts of North America and Asia. It is also sometimes referred to as Eryngo-leaved Liverwort. The extract is, in accordance with the present invention, an alcohol extract of the plant Cetraria. In the preferred form of the invention presently known, the pharmaceutical preparation is prepared by making a grain or ethyl alcohol extract of the dried herb or plant Cetraria. The alcohol extract is used to heal the ulcers by orally administering the alcohol extract of the plant Cetraria to the patient suffering from the gastro intestinal ulcers. In a preferred practice of the present invention, the alcohol extract is administered to the patient orally a predetermined amount of time before each meal.

The pharmaceutical preparation in a preferred embodiment is produced as a strong grain or ethyl alcohol extract of the plant Cetraria. In a preferred method of practicing the invention, 190 proof ethyl alcohol was used, although it is understood that solvents of other alcoholic proof may be used. In the preferred embodiment, dried cuttings were placed in the 190 proof grain or ethyl alcohol and allowed to stand for approximately two weeks. However, it is understood that other suitable solvents having similar properties may be used after testing to ensure safety and effectiveness for the intended purpose of the present invention.

In the preferred method of practicing the invention, the Cetraria plant remained in the solvent of ethyl alcohol for approximately two weeks. However, it is understood that other suitable periods of time, shorter or longer than two weeks, may be used. After two weeks it was filtered, and the extract so obtained was used as the pharmaceutical preparation for treating the ulcer patients.

I used the alcohol extract of the Cetraria plant, prepared as described, to treat hundreds of ulcer sufferers in Europe. Most of these ulcer sufferers had ulcers of the stomach and/or duodenum, although a few cases of ulcerative colitis which affects the colon were also effectively treated by the pharmaceutical preparation of the present invention. One of my patients who suffered from stomach ulcers for 35 years took the alcohol extract of the Cetraria plant only four times and the pain completely disappeared without reoccurrence, resulting from continued treatment. In use of the pharmaceutical preparation of the present invention, there is no need for the patient to be on a diet during treatment and no diet of any kind is required. The pain of the ulcer disappears shortly after the initiation of the treatment with the pharmaceutical preparation of the present invention. No side effects were noticed in any of the several hundred patients treated with the pharmaceutical preparation in accordance with the present invention.

In treating ulcers of the stomach and duodenum in Europe in accordance with my pharmaceutical preparation invention, I administered the alcohol extract of the Cetraria plant in the form of drops a set period of time before each meal, three times a day. In actual practice, I prescribed thirty (30) drops of the Cetraria plant extract to be taken with one tablespoon of boiled water as the dosage 40 minutes before each meal, three times a day. In most cases or on the average, the Cetraria plant extract was taken for seven days. Of course, it will be understood by those skilled in the art that the length of time of treatment and the exact dosage may vary especially where the patient's size, age and other physical characteristics may vary. In addition, the exact times of taking the dosages may be varied and the number of times a day in which it is taken. However, I have found it to be most effective to take it a predetermined amount of time before each meal such as thirty (30) to fifty (50) minutes before a meal, when the stomach is empty. It is understood that flavoring or other substances may be combined with the pharmaceutical preparation of my invention in order to make it more palatable.

It is believed that the pharmaceutical preparation of the present invention regulates the secretion of stomach acid which is at least partially responsible for its effectiveness in healing ulcers of the stomach and duodenum.

The present invention may be embodied in other specific forms without departing from the spirit or essential attributes thereof and, accordingly, reference should be made to the appended claims, rather than to the foregoing specification as indicating the scope of the invention.

I claim:

1. A method of treating pain and suffering of gastro intestinal ulcers by orally administering a grain or ethyl alcohol extract of the dried herb Cetraria.

2. A method in accordance with claim 1 wherein said alcohol extract of the herb Cetraria is administered orally approximately 30 to 50 minutes before a meal.

* * * * *